US005538855A

United States Patent [19]
Orfao de Matos Correira E Vale

[11] Patent Number: 5,538,855
[45] Date of Patent: Jul. 23, 1996

[54] PROCEDURE FOR THE SIMULTANEOUS QUANTIFICATION, IN A SINGLE MEASUREMENT, OF THE MAJOR TYPES OF HUMAN LYMPHOCYTES AND THEIR SUBSETS

[75] Inventor: José A. Orfao de Matos Correira E Vale, Salamanca, Spain

[73] Assignee: Universidad de Salamanca, Salamanca, Spain

[21] Appl. No.: 163,540

[22] Filed: Dec. 9, 1993

[30] Foreign Application Priority Data

Dec. 10, 1992 [ES] Spain .................................. 9300001

[51] Int. Cl.$^6$ ..................... G01N 33/533; G01N 33/536; G01N 33/577
[52] U.S. Cl. ........................ 435/7.24; 435/7.25; 436/536; 436/546; 436/172; 436/800
[58] Field of Search ................................. 435/7.25, 7.24; 436/536, 546, 172, 800, 805; 356/337, 39

[56] References Cited

U.S. PATENT DOCUMENTS 4,499,052  2/1985  Fulwyler ................................. 422/52

FOREIGN PATENT DOCUMENTS

| 0132064 | 1/1985 | European Pat. Off. . |
| 0219309 | 4/1987 | European Pat. Off. . |
| 0257559 | 3/1988 | European Pat. Off. . |
| 0317156 | 5/1989 | European Pat. Off. . |
| 0337586 | 10/1989 | European Pat. Off. . |
| 0470810A1 | 2/1992 | European Pat. Off. . |

OTHER PUBLICATIONS

Rabian–Betzog, C. et al, "Characterization of lymphocyte subpopulations in cord blood", Bone marrow Transplant, vol. 9(Supplement 1), pp. 64–67, Jun. 1992

Mandy, F. F., et al, "A simultaneous three–color T cell subsets analysis with single laser flow cytometers using T cell gating protocol", Journal of Immunological Methods, vol. 156, pp. 151–162, Dec. 8, 1992.

Richards, S. J. et al, "Immunophenotypic Dissection of Normal Peripheral Blood NK Associated (NKa) Subpopulations by Flow Cytometry: Morphological Features and Relationships Between Membrane NKa (CD11b, CD16, CD56 and CD57) and T–Cell (CD2, CD3, TCR, CD5, CD7, CD8 and CD38) Associated Determinant Expression", Leukemia and Lymphoma, vol. 2, pp. 111–126, 1990.

*Lymphocyte Subset Reference Ranges in Adult Caucasians*, T. Reichert, et al., Clinical Immunology and Immunopathology 60, 190–208, (1991).

*Primary Examiner*—James C. Housel
*Assistant Examiner*—Nancy J. Parsons
*Attorney, Agent, or Firm*—Wigman, Cohen, Leitner & Myers

[57] ABSTRACT

Procedure for the simultaneous quantification, in a single measurement, of the major types of human lymphocytes and their subsets. It includes: incubation of the sample with five different monoclonal antibodies conjugated with three different fluorochromes; measurement by flow cytometry of the three fluorescent emissions; and analysis of the results obtained by means of multiparametric analysis to determine the presence/absence of a certain fluorescence in a cell and its intensity in each cell.

9 Claims, 2 Drawing Sheets

PROCEDURE FOR THE SIMULTANEOUS QUANTIFICATION, IN A SINGLE MEASUREMENT, OF THE MAJOR TYPES OF HUMAN LYMPHOCYTES AND THEIR SUBSETS

BACKGROUND OF THE INVENTION

Although not exclusively, this invention is mainly related to a procedure for the simultaneous quantification of the major types of human lymphocytes (T, B, and NK cells) and their subsets (CD3+/CD4+, CD3+/CD8+, etc) up to a total of 12 lymphoid subpopulations by means of a quick, cost effective, sensitive and specific single measurement capable of being analyzed in a flow cytometer equipped with a single laser for research or diagnostic, prognostic and therapeutic purposes.

Lymphocytes are the cells responsible for immunosurveillance as well as for the specificity of immune defense in humans. The immunophenotyping of lymphoid subpopulations by combining the use of monoclonal antibodies and flow cytometry provides objective and sensitive measurements of both the distribution of the lymphoid subpopulations and their intensity of positivity for a certain antigen.

Both types of information have rapidly attracted the attention of professionals from different areas of Medicine such as Cell Biology, Immunology and Hematology, as the measurement of different lymphoid subsets has proved to be of great diagnostic and prognostic value in different pathologic conditions.

Of all these applications, one whose usefulness should be pointed out is that of the enumeration of CD4+ T-cells in those individuals who display serum antibodies against the human immunodeficiency virus (HIV) responsible for the acquired immunodeficiency syndrome (AIDS). This measurement represents at present one of the most important prognostic criteria that should be taken into account when analyzing these patients' progress.

The clinical relevance of this kind of measurement has largely contributed to the fact that over the past few years there has been an enormous increase in the need for appropiate quality control procedures when analyzing lymphoid subpopulations by flow cytometry in order to eliminate technical artifacts that may lead to erroneous results.

As a result of these studies dealing with the standardization of lymphoid subset measurement using flow cytometry, several research groups, scientific associations and public institutions have published documents with recommendations and guidelines for everyone to follow when immunophenotyping human lymphocytes by means of flow cytometry. These documents recognize the need for systematic identification of: 1) the proportion and purity of the lymphocytes analyzed, i.e., the proportion of lymphocytes not included in the analysis as well as the proportion of the events analyzed that correspond to lymphocytes; and 2) the total number of T, B and NK cells as well as CD3+/CD4+ and CD3+/CD8+ T-cell subsets. This means that a minimal panel of monoclonal antibodies must be used which in turn means that a high number of measurements must be carried out per sample.

As an example, in 1992 the CDC (Center for Disease Control, USA) recommended the use of five different measurements combining two monoclonal antibodies with different fluorochromes for the enumeration of CD4+ T-cells in HIV+ patients in order to fulfill the two objectives mentioned above:

1) CD45/CD14 for the study of the purity and the proportion of lymphocytes analyzed.

2) CD3/CD19 for the identification of the total number of T-lymphocytes (CD3+/CD19−) and the total number of B-lymphocytes (CD3−/CD19+).

3) CD3/CD56 for the characterization of NK-cells (CD56+/CD3−).

4) CD3/CD4 for the identification of CD3+/CD4+ T-cells which are related to helper/induction functions within the immune system.

5) CD3/CD8 for the identification of CD3+/CD8+ T-cells witch are associated with suppresor/cytotoxic immunologic functions.

Until now, no procedure has been described that allows direct and simultaneous analysis of the total number of T, B, NK, CD3+/CD4+ and CD3+/CD8+ populations in a single measurement, eliminating the need to perform up to five different measurements using ten monoclonal antibodies in double-staining combinations.

SUMMARY AND OBJECTS OF THE INVENTION

Thus one of the aims of this invention is to propose a solution for the simultaneous study, in a single measurement, of 12 lymphoid subsets, including all of the T, B, NK, CD3+/CD4+ and CD3+/CD8+ lymphocytes.

Another aim of the invention is the simultaneous assessment of contamination by non-lymphocytes present in the elements analyzed.

The procedure of this invention consists of the use of a mixture of five monoclonal antibodies conjugated with three different fluorochromes: CD19 and CD8 conjugated with one fluorochrome (FL1), for instance fluorescein isothiocyanate (FITC); CD3 and CD56 conjugated with another fluorochrome (FL2), such as phycoerythrin (PE); and CD4 conjugated with a third fluorochrome (FL3), such as Peridinin Chlorophyll Protein or TriColor tm the phycoerythrin/cyanine 5 tandem of fluorochromes.

Sample preparation, cell staining with monoclonal antibodies, selection of lymphocytes, as well as the calibration and adjustment of the flow cytometer are performed in accordance with widely described and recommended methods for the immunophenotyping of lymphoid subpopulations.

For the analysis of the results and for the exact quantification of each subpopulation, different software programs can be used, of these PAINT-A-GATE PLUS tm was especially useful. In the analysis both the negativity/positivity and the intensity of positivity for each monoclonal antibody are taken into account.

BRIEF DESCRIPTION OF THE DRAWINGS

An explanation of the procedure for the analysis of the results obtained from the measurement performed with the flow cytometer is described below in combination with accompanying figures, where.

It is a reproduction of the image obtained by computer, where the different lymphocyte subpopulations appeared identified by different colors, which have been substituted in the attached drawing by dots of different thickness, with the following key:

Grey - dots of 0.1 mm - reference No. 1
Green - dots of 0.2 mm - reference No. 2
Blue - dots of 0.3 mm - reference No. 3
Black - dots of 0.4 mm - reference No. 4
Royal Purple - dots of 0.5 mm - reference No. 5
Violet - dots of 0.2 mm - reference No. 6
Orange - dots of 0.3 mm - reference No. 7
Red - dots of 0.4 mm - reference No. 8
The different subpopulations were identified as follows:
Total T-cells (violet+red+orange+black).
Total NK-cells (purple+blue).
Total B-cells (green)
CD3+/Cd4+ cells (violet+a small proportion of black).
CD3+/CD8+ (black+orange).
CD3–/CD8 dim+cells (orange).
CD3+/CD8 strong+cells (black).
CD3+/CD4–/CD8– cells (red)
CD8– NK-cells (purple)
CD8+ NK-cells (light blue).
CD3+ /CD8– cells (violet+red).
CD3+/CD4+/CD8+ cells (a small proportion of the black elements that has not been identified with a specific color because the software program has no more possibilities for different colors).

Figure 2:
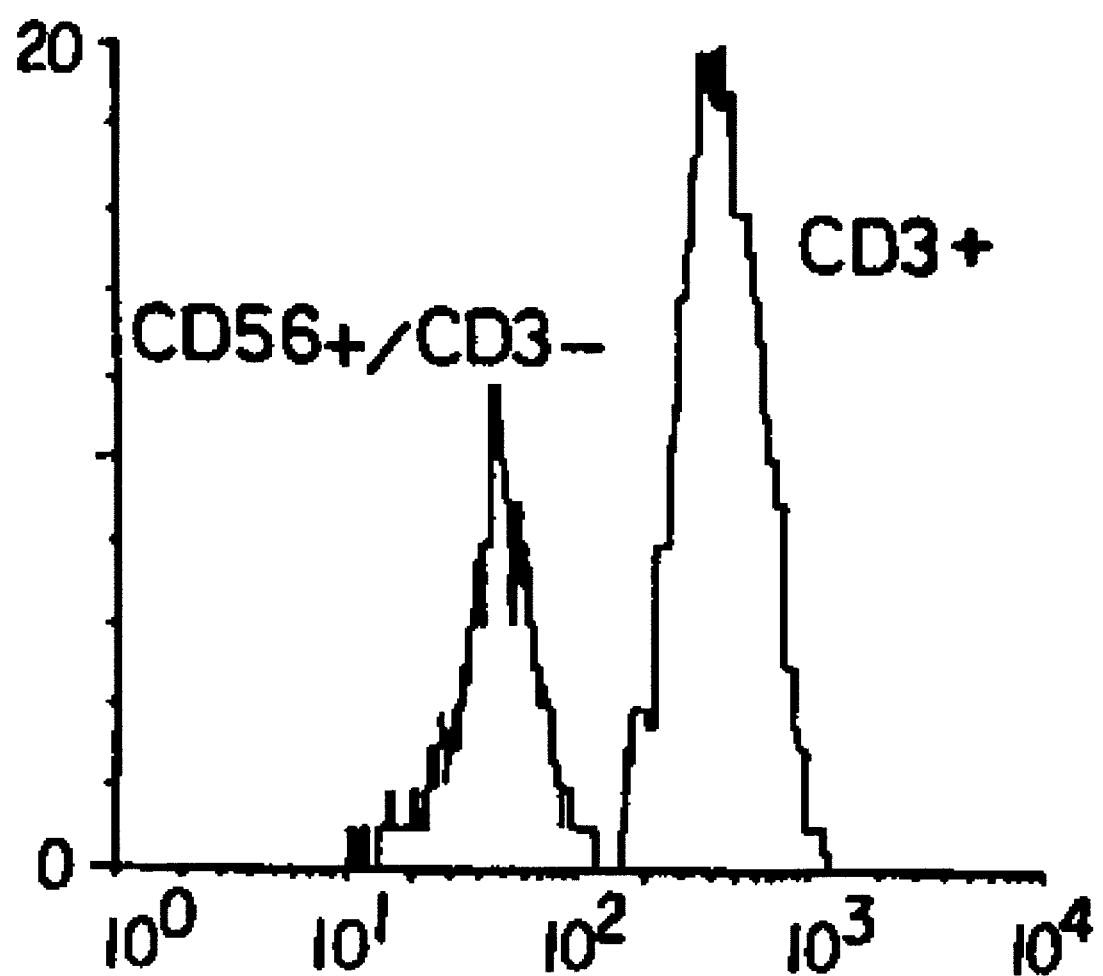

FIG. 2 is a diagrammatic representation of the fluorescence intensity for CD56 and CD3 marked with the same fluorochrome in lymphocytes NK and T, respectively. Non-lymphoid elements are shown in grey.

B-lymphocytes are the only major population of FL1+ lymphocytes (CD19+ or CD8+) that lacks the expression of CD3 and CD56 (FL2), thus being the only FL1+/FL2– lymphocytes when considering the FL1/FL2 bidimensional space.

In addition, among T, B, and NK cells, the CD19 antigen is specific for B-lymphocytes, being present in all these cells, which in turn are CD8–.

Figure 1:
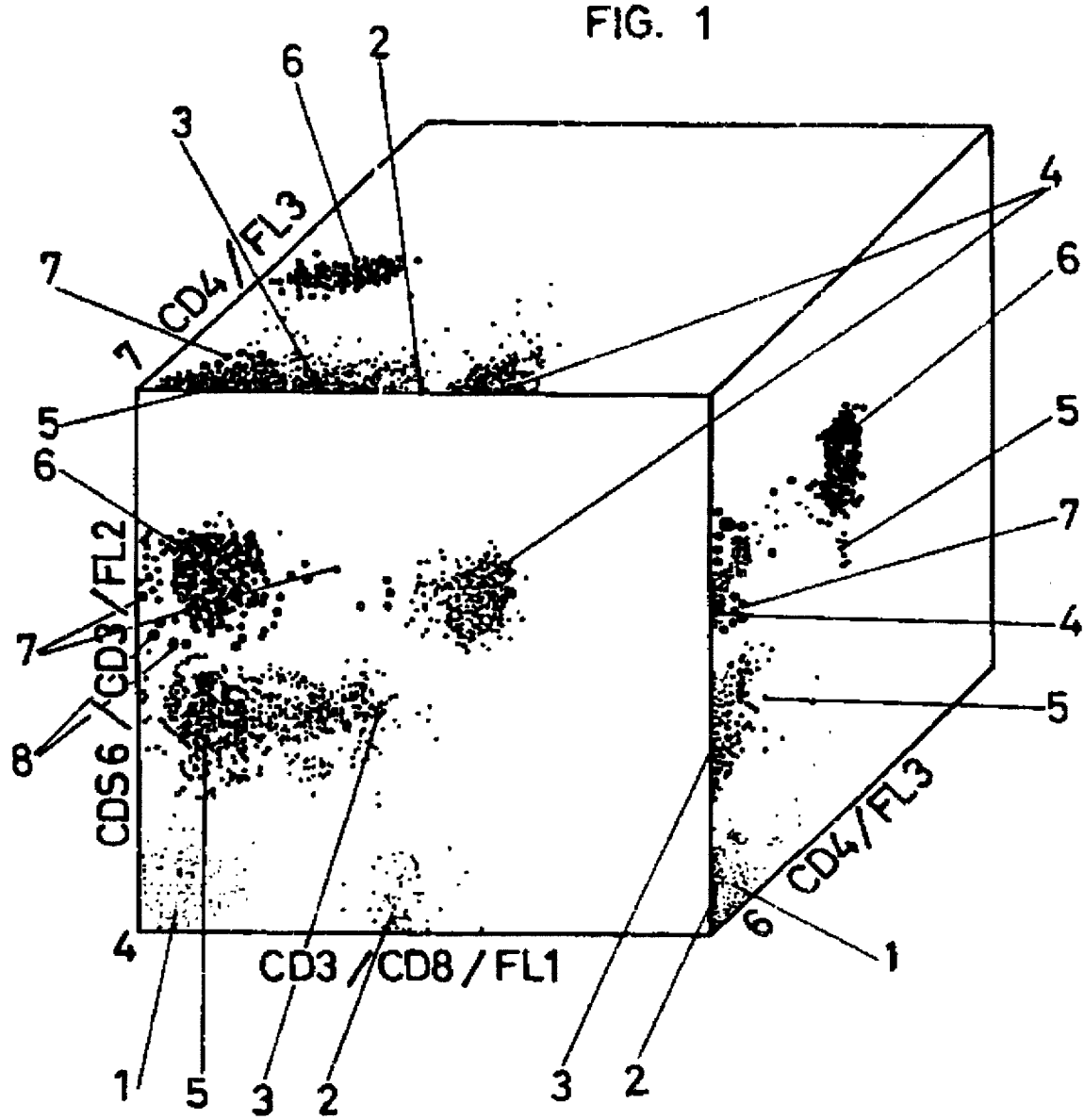
FIG. 1 is a FL1, FL2 and FL3 representation of the majority of the identified subpopulations.

Accordingly we can state that the FL1+/FL2– cells correspond to the total number of B-cells (FIG. 1).

The separation between T (FL2+ because they are CD3+) and NK cells (FL2+ because they are CD56+/CD3–) is clearly established when the intensity of FL2 fluorescence/cell is considered. This is due to the fact that the intensity of CD3 fluorescence in lymphocytes is constantly different from that of CD56 fluorescence in NK cells when the same fluorochrome is used for the detection of both antigens by flow cytometry, there being no overlap between these two lymphoid populations in the axis that in this case reflects the amount of FL2 (FIG. 2).

Thus, when the FL1/FL2 bidimensional space is exclusively considered, total B (CD19+/CD3–/CD56–), T (CD3+/CD19–/CD56+ or –) and NK cells (CD56+/CD3–/CD19–) are measured (FIG. 1).

Moreover, it allows us to determine the purity of the lymphocytes analycez since the sum of total CD19+, CD3+ and CD56+/CD3– cells represents the total number of lymphocytes present in the sample analyzed and thus the CD19–/CD3–/CD56– elements are non-lymphoid cells or events.

Starting with CD8-FL1 allows other T and NK cell subpopulations to be identified: 1) CD3+/CD8+ T-lymphocytes; 2) CD3+/CD8– T-lymphocytes; 3) CD56+/CD3–/CD8+ NK cells; and 4) CD56+/CD3–/CD8– NK cells.

NK cells can also be identified by adding either CD16 monclonal antibody with an identical flurochrome to that of CD3 and CD56 or by simply replacing CD56 with CD16.

In addition, regarding CD3+/CD8+ T-lymphocytes, CD3+ T-cells that express CD8 at low intensity can be identified and separated from those that show strong CD8 expression (FIG. 1).

Staining with CD4 conjugated with a third fluorochrome (FL3) allows the identification of the subset of CD3+/CD4+ T-lymphocytes and the possible presence or absence in the sample of CD3–/CD4+ cells lacking the CD19 antigen; the latter cells correspond to the contamination of monocytes (FIG. 1).

Finally, when the reactivities for CD3, CD8 and CD4 are simultaneously taken into account, another two T-cell subpopulations are identified: 1) CD3+/CD4–/CD8– T-lymphocytes; and 2) CD3+/CD4+/CD8+ T-lymphocytes.

The invention can be used for both normal and pathologic samples for all purposes in which the analysis of lymphoid populations is required, particularly for research, diagnostic and prognostic purposes as well as for therapeutic evaluation.

As can be concluded from what has been previously explained, the fluorochromes used in FL1, FL2 and FL3 can be modified. Moreover, it is understood that this invention includes variations that omit a third fluorescence such as the CD19-FL1/CD8-FL1/CD3-FL2/CD56-FL2 and the CD19-FL1 /CD4-FL1 /CD3-FL2/CD56-FL2 combinations.

Among other advantages, an important decrease in the time, the costs and the variability of the analysis of lymphoid subpopulations is obtained with this invention.

In addition, it should be taken into consideration that its capacity to perform this five-fold combination provides detailed information about a total of 12 lymphoid subpopulations, this being of great interest in order to systematically determine the distribution of lymphoid subsets and their possible role in different pathologic conditions. Moreover, it allows the direct quantification of the non-lymphoid elements that are present in the analysis.

Next, the invention will be illustrated by the following example, which is not limitative of its possibilities:

DESCRIPTION OF A PREFERRED EMBODIMENT

EXAMPLE

1. Material and Methods

Peripheral blood (PB) was obtained from 10 healthy volunteers in the presence of liquid EDTA (K3) by venipunction and maintained at room temperature until processed. The analysis of PB lymphoid subpopulations was performed within five hours using a whole lysed blood and direct immunofluorescence technnique measured by flow cytometry.

2. Sample Preparation

Six test-tubes containing 100 μ of PB and different combinations of directly-conjugated monoclonal antibodies purchased from Becton/Dickinson (San José, Calif., USA) were prepared for each of the samples.

The specificities of the combinations of monoclonal antibodies used were as follows:

1) Hle-FITC (CD45)/LeuM3-PE (CD14)/Leu4-PerCP (CD3);

2) Leu4-FITC (CD3)/Leu3a-PE (CD4);

3) Leu4-FITC (CD3)/Leu2a-PE (CD8);

4) Leu4-FITC (CD3)/Leu12-PE (CD19);

5) Leu4-FITC (CD3)/Leu19-PE (CD56);

6) Leu12-FITC (CD19)/Leu2a-FITC (CD8)/Leu4-PE (CD3)/Leu19-PE (CD56)/Leu3a-PerCP (CD4).

The last test-tube was referred to as the PANEL tube.

For each of the samples a test-tube containing isotype-matched mouse immunoglobulins was used as a negative control in order to establish the cursors for positivity.

The test-tubes were slowly vortexed and incubated for 10–15 minutes at room temperature in the dark. Immediately after this incubation period 2 ml of FACS lysing solution (Becton/Dickinson) were added per tube, followed by 4–5 seconds of vortexing. Afterwards, the cells were incubated for another 10 minutes in the dark (room temperature). Samples were then centrifuged at 300 g for 5 minutes (4° C.). The supernatant was aspirated and the cell pellet resuspended by vigorous vortexing (1–2 second). Then, 1 ml of phosphate buffer saline solution (PBS) containing 1 g of albumin bovine (Sigma Chemicals, St. Louis, Mo., USA) was added to each tube. Another centrifugation was then performed (300 g, 5 minutes), the cells being finally resuspended in 0.5 ml of PBS containing 1 g of albumin bovine and stored at 4° C. until they were analyzed in the flow cytometer.

3. Data Acquisition and Analysis

Measurements were performed on a FACScan flow cytometer (Becton/Dickinson) equipped with an argon ion laser tuned at 488 nm and 15 mWatts. The instrument was calibrated using CALIBRITE beads (Becton/Dickinson) and PB lymphocytes stained in three different tubes for:

1) CD3 (Leu4-PerCP);

2) CD4 (Leu3a-FITC)/CD8 (Leu2a-PE)

3) CD4 (Leu3a-FITC)/CD8 (Leu2a-PE)/CD3 (Leu4-PerCP).

Regarding day-to-day calibration, an identical separation was obtained between the fluorescence peaks of the positive and negative lymphoid subpopulations for FL1 (CD4-FITC), FL2 (CD8-PE strong positive) and FL3 (CD3-PerCP), variability being in all cases lower than 1.5%.

Analysis was performed with the PAINT-A-GATE Plus software program (Becton/Dickinson) using its capacity for log transformation of side scatter (SSC) in order to obtain a better separation between the cell populations identified by SSC/FSC (side scatter/forward scatter). In order to establish the ideal FSC/SSC lymphocyte gate the CD45-FITC/CD14-PE (LeucoGATE) test-tube was used according to previous established guidelines.

In all cases the percentage of CD45 negative, CD14 positive and CD45-dim positive cells inside the FSC/SSC lymphocyte gate as well as the percentage of lymphocytes not included in the gate were calculated.

The percentage of positive cells for each antigen was calculated from the selected FSC/SSC lymphocyte gate, the sum of the percentage of CD3+, CD19+ and CD3–/CD56+ cells being considered as 100% of the lymphocytes.

Comparison of individual variables was performed through analysis of variance (ANOVA) at a level of significance of 5% . The LSD Fisher test was used for comparisons between two groups. Pearson's coefficients of correlation were calculated for the relationship between results obtained with the PANEL tube and with the other test-tubes for %CD3+, %CD19+, %CD3–/%CD56+, %CD3+/%CD4+ and CD3+/%CD8+.

The results obtained are shown in the accompanying figures explained above.

What I claim is:

1. Process for the simultaneous quantification, in a single measurement of 12 B, T and NK lymphoid subpopulations, including the total number of B, T and NK cells as well as $CD3^+/CD8^+$ T-cell subpopulations, and the determination of contamination by monocytes ($CD4^{dim+}/CD3^-$) and other non-lymphoid elements ($CD3^-/CD4^-/CD8^-/CD19^-/CD56^-$) comprising the following steps:

a) incubating the sample with five different fluorochrome labeled monoclonal antibodies specific for the CD3–, CD4–, CD8–, CD19–, CD56– antigens within the lymphocytic cluster of differentiation (CD) wherein the CD8 and CD19 monoclonal antibodies are conjugated with the same (type of fluorochrome, CD3 and CD56 monoclonal antibodies are conjugated with a different fluorochrome and the CD4 antibody is conjugated with a third fluorochrome and wherein the monoclonal antibodies are specific within the cluster of differentiation (CD);

b) passing the sample through a flow cytometer;

c) measuring the three different fluorescent emissions by means of flow cytometry in a single measurement; and d) analyzing the results obtained using multiparametric analysis to determine the presence/absence and the intensity of fluorescence in each cell of each of the different fluorochromes used.

2. The method of claim 1 wherein the sample obtained is selected from normal or pathogenic samples obtained in vivo or obtained after being stored or treated in vitro are used.

3. The method of claim 1 wherein including the step of simultaneously determining contamination of the cells analyzed by monocytes and other non-lymphoid elements said monocytes being identified by being dim positive for CD4 and $CD3^-$ labeled antibodies and other non-lymphoid elements being $CD3^-$, $CD4^-$, $CD8^-$, $CD19^-$, and $CD56^-$.

4. The process of claim 1 wherein the fluorochromes are selected from the group consisting of fluoroscein isothiocyanate, phycoerythrin, peridinin chlorophyll protein and phycoerythrin/cyanine 5 tandem of fluorochromes.

5. The process of claim 1, wherein the first fluorochrome is fluorescein isothiocyanate; the second fluorochrome is phycoerythrin; and the third fluorochrome is peridinin chlorophyll protein or phycoerythrin/cyanine 5 tandem of fluorochromes.

6. The process of claim 1, wherein the identification of NK cells is obtained by adding either monoclonal antibodies specific for the CD16 antigen with a fluorochrome identical to the fluorochrome conjugated to the monoclonal antibodies specific for the CD3 and CD56 antigens or by simply replacing the monoclonal antibodies specific for the CD56 antigen with monoclonal antibodies specific for CD16 antigen, again the fluorochrome for the antibodies specific for the CD16 antigen is identical to the fluorochrome of the antibodies specific for the CD56 antigen.

7. The process of claim 1, wherein monoclonal antibodies specific for the CD4 antigen conjugated with the third fluorochrome can be replaced by monoclonal antibodies specific for the CD8 or CD3 antigens conjugated with the third fluorochrome.

8. A kit for the simultaneous determination in a single measurement of 12 B, T and NK lymphoid subpopulations, the total number of B, T and NK cells as well as the CD3+/CD4+ and CD3+/CD8+ T-cell subpopulations, the kit comprising monoclonal antibodies specific for CD3, CD4, CD8, CD19 and CD56 antigens, said antibodies are coupled to at least three different fluorochromes wherein monoclonal antibodies specific for the CD8 and CD19 antigens are conjugated with a first fluorochrome, monoclonal antibodies specific for the CD3 and CD56 antigens are conjugated with a second fluorochrome and monoclonal antibodies specific for the CD4 antigen are conjugated with a third fluorochrome.

9. The kit of claim 8 wherein the first, second and third fluorochromes are selected from the group consisting of fluorescein isothiocyanate, phycoerythrin, peridinin chlorophyll protein and phycoerythrin/cyanine 5 tandem of fluorochromes.

* * * * *